（12）United States Patent
Hathaway et al.

(10) Patent No.: US 7,259,136 B2
(45) Date of Patent: Aug. 21, 2007

(54) COMPOSITIONS AND METHODS FOR TREATING PERIPHERAL VASCULAR DISEASE

(75) Inventors: David R. Hathaway, Lincoln, NE (US); Thomas R. Coolidge, Falls Village, CT (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 597 days.

(21) Appl. No.: 10/091,258

(22) Filed: Mar. 5, 2002

(65) Prior Publication Data

US 2003/0073626 A1      Apr. 17, 2003

Related U.S. Application Data

(60) Continuation-in-part of application No. 09/851,738, filed on May 9, 2001, which is a division of application No. 09/302,596, filed on Apr. 30, 1999, now Pat. No. 6,284,725.

(51) Int. Cl.
*A61K 38/28* (2006.01)
*A61K 38/26* (2006.01)

(52) U.S. Cl. .................. 514/2; 514/3; 514/21; 530/308; 530/324; 424/198; 424/278.1

(58) Field of Classification Search .................... 514/2, 514/21, 3; 530/308, 324; 424/198, 278.1, 424/278

See application file for complete search history.

(56) References Cited

U.S. PATENT DOCUMENTS

| 4,196,196 A | 4/1980 | Tiholiz |
| 5,955,594 A | 9/1999 | Mishra |
| 6,107,329 A | 8/2000 | Hoover et al. |

FOREIGN PATENT DOCUMENTS

| EP | 0708179 A2 | 4/1996 |
| WO | WO94/15925 Y | 7/1994 |
| WO | WO98/08531 A1 | 3/1998 |
| WO | WO98/08531 X | 3/1998 |
| WO | WO98/08873 A | 3/1998 |
| WO | WO98/30231 | 7/1998 |
| WO | WO98/43658 A | 10/1998 |
| WO | WO 00/16796 A2 | 3/2000 |
| WO | WO 16797 A | 3/2000 |

OTHER PUBLICATIONS

Sterre, V. et al. (1998) Exendin-(9-39) is an inverse agonist of the murine glucagon-like peptide-1 receptor: implications for basal intracellular cyclic adenosine 3',5'-monophosphate levels and beta-cell glucose competence. Endocrinol. vol. 139, 4448-4454.*

Apstein, "Glucose-Insulin-Potassium for Acute Myocardial Infarction; Remarkable Results From a New Prospective, Randomized Trial," CIRCULATION, vol. 98, Nov. 24, 1998, pp. 2223-2226; XP000960510 (no copy).

Jeffrey I. Weitz, John Byrne, G. Patrick Clagett, Michael E. Farkouh, John M. Porter, David L. Sackett, D. Eugene Strandness, Jr., Lloyd M. Taylor; "Diagnosis and Treatment of Chronic Arterial Insufficiency of the Lower Extremities: A Critical Review"; *American Heart Association*; 1996, pp. 1-43; Dallas, TX.

Simon Green; "Phosphorus 31 nuclear magnetic resonance spectroscopy suggests a mitochondrial defect in claudicating skeletal muscle"; *Journal of Vascular Surgery*; May 2001, vol. 33, No. 5, pp. 1-2, Mosby.

Muredach P. Reilly and Emile R. Mohler III; "Cilostazol: Treatment of Intermittent Claudication"; *The Annals of Pharmacotherapy*; Jan. 2001, vol. 35, pp. 48-56.

Carlos Iribarren, Andrew J. Karter, Alan S. Go, Assiamira Ferrara, Jennifer Y. Liu, Stephen Sidney and Joseph V. Selby; "Glycemic Control and Heart Failure Among Adult Patients With Diabetes"; *American Heart Association*; 2001, pp. 2668-2673; American Heart Association, Inc.

Hari K. Bhat, William R. Hiatt, Charles L. Hoppel, Eric P. Brass; "Skeletal Muscle Mitochondrial DNA Injury in Patients With Unilateral Peripheral Arterial Disease"; *American Heart Association, Inc.*, 1999, pp. 807-812; American Heart Association, Inc.

Robert D. Abbott, Richard P. Donahue, William B. Kannel, Peter W.F. Wilson; "the Impact of Diabetes on Survival Following Myocardial Infarction in Man vs. Woman"; *JAMA*, Dec. 16, 1988, vol. 260, No. 23, pp. 3456-3460; National Heart, Lung and Blood Institute, Bethesda, MD.

Frederick N. Brand, Robert D. Abbott, and William B. Kannel; "Diabetes, Intermittent Claudication, and Rick of Cardiovascular Events"; Jul. 1988; *Diabetes*, vol. 38, pp. 504-509; National Heart Lung and Blood Institute, Bethesda, Maryland.

R. Stuart Gray, Richard R. Fabsitz, Linda D. Cowan, Elisa T. Lee, Barbara V. Howard and Peter J. Savage; "Risk Factor Clustering in the Insulin Resistance Syndrome"; *American Journal of Epidemiology*; 1998, vol. 148, No. 9, pp. 869-878, The Johns Hopkins University School of Hygiene and Public Health.

David L. Dawson, Bruce S. Cutler, William R. Hiatt, Robert W. Hobson II, John D. Martin, Enoch B. Bortey, William P. Forbers, and D. Eugene Strandness, Jr.; "A Comparison of Cilostazol and Pentoxifylline for Treating Intermittent Claudication"; 2000, pp. 523-530; by Excerpta Medica, Inc.

William R. Hiatt, Dilsher Nawaz, and Eric P. Brass; "Carnitine metabolism during exercise in patients with peripheral vascular disease"; 1987; pp. 2383-2387; *The American Physiological Society*; Colorado School of Medicine, Denver, Co.

Thomas L. Clanton and Paul F. Klawitter, "Physiological and Genomic Consequences of Intermittent Hypoxia Invited Review; Adaptive responses of skeletal muscle to intermittent hypoxia: the known and the unknown"; 2001; *The American Physiological Society*; pp. 2476-2487; The American Physiological Society.

(Continued)

*Primary Examiner*—Jon Weber
*Assistant Examiner*—Samuel W. Liu

(57) ABSTRACT

The present invention relates to methods of treating intermittent claudication comprising administering glucagon-like peptide-1 (GLP-1) molecules to subjects suffering therefrom.

11 Claims, No Drawings

OTHER PUBLICATIONS

M.D. Boska, J.A. Nelson N. Sripathi, I.I. Pipinos, A.D. Shepard, and K.M.A. Welch; "P MRS Studies of Exercising Human Muscle at High Temporal Resolution"; 1999, pp. 1145-1151, Wiley-Liss, Inc.

Robert L. Dupont, Keith E. Saylor; "Marijuana and Benzodiazepines in Patients Receiving Methadone Treatment"; *JAMA* Jun. 1989, vol. 261, No. 23; pp. 3409; Institute for Behavior and Health, Inc.

Robert Matz; "Does Control of Diabetes Prevent Vascular Complications?"; *JAMA*; Jun. 1989, vol. 261, No. 23, p 3409; Institute for Behavior and Health, Inc.

Norman J. Sissman, Robert Wood Johnson; Patent Ductus Arteriosus, Prematurity, and Respiratory Distress Syndrome; *JAMA*, Jun. 1989, vol. 261, No. 23, p. 3410; University of Medicine and Dentistry of New Jersey, New Brunswick, NJ.

J.F. Scott, C.S. Gray, J.E. O'Connell and K.G.M.M. Alberti; "Glucose and insulin therapy in acute stroke; why delay further?"; *QJM*, 1998; 91:511-515.

Partial European Search Report dated Jan. 13, 2005 issued in European Patent Application No. 04027507.5.

Diaz, Rafael, et al, "Metabolic Modulation of Acute Myocardial Infarction the ECLA Glucose-Insulin-Potassium Pilot Trial,", Circulation (1998) pp. 2227-2234, 98.

Ryan, Thomas J., et al, "ACC/AHA Guidelines for the Management of Patients with Acute Myocardial Infarction" J. Am Coll. Cardiol. (1996) pp. 1328-1428, 28.

Voll, C.L., et al. "Postischemic Insulin Reduces Spatial Learning Deficit Following Transient Forebrain in Ischemia Rats", Stroke (1998) pp. 646-651, 20.

\* cited by examiner

COMPOSITIONS AND METHODS FOR TREATING PERIPHERAL VASCULAR DISEASE

CROSS REFERENCE TO RELATED APPLICATIONS

This application is a continuation-in-part of U.S. application Ser. No. 09/851,738, filed May 9, 2001, now issued as U.S. Pat. No. 6,982,248, which is a divisional of U.S. application Ser. No. 09/302,596, filed Apr. 30, 1999, now issued as U.S. Pat. No. 6,284,725, the entire disclosure of both of which are incorporated by reference herein.

TECHNICAL FIELD OF THE INVENTION

The present invention relates to endocrinology, physiology and pharmacology. The invention also relates to metabolic intervention with GLP-1 to therapeutically improve the function of ischemic and reperfused tissue. More particularly, it relates to methods and compositions for treating subjects suffering from intermittent claudication, typically associated with peripheral vascular disease (PVD).

BACKGROUND OF THE INVENTION

Cellular damage to aerobic organ tissues is well recognized as a consequence of ischemia, whether endogenous as in the case of spontaneous coronary artery occlusion, or iatrogenic such as with open heart, coronary bypass surgery, or transplant procedures with the hear or other organs such as the lung, liver, kidney, pancreas and gastrointestinal tract. The degree and duration of the ischemia causing events are relevant to the amount of cell death and/or reversible cellular dysfunction. It is also known that much of the tissue damage in fact occurs upon reperfusion (i.e. resumption of blood flow) and re-oxygenation of the previously anoxic tissue.

As a side product of normal aerobic respiration, electrons are routinely lost from the mitochondrial electron transport chain. Such electrons can react with molecular oxygen to generate the reactive free radical superoxide which through other reaction steps in the presence of hydrogen peroxide and iron produces the extraordinarily reactive and toxic hydroxyl radical. Metabolically active aerobic tissues possess defense mechanisms dedicated to degrading toxic free radicals before these reactive oxygen species can interact with cellular organelles, enzymes, or DNA, the consequences of which could, without such protective mechanisms, be cell death. These defense mechanisms include the enzymes superoxide dismutase (SOD) which disproportionates superoxide, catalase which degrades hydrogen peroxide, and the peptide glutathione which is a non-specific free radical scavenger.

While not fully understood, it is believed that with ischemia of metabolic tissues and subsequent reperfusion, a complex group of events occurs. Initially during the ischemic period, intracellular anti-oxidant enzyme activity appears to decrease, including that of SOD, catalase, and glutathione. There is also an indication that the level of xanthine oxidase activity concomitantly increases in vascular endothelial tissue during the ischemic event. The combination of enhanced ability to produce oxygen free radicals (via enhanced xanthine oxidase activity) and reduced ability to scavenge the same oxygen radicals (via reduced SOD, catalase and glutathione activity) greatly sensitizes the ischemic cell to an oxidative burst, and hence damage, should these cells be subsequently reperfused with blood and therefore oxygen. This oxidative burst occurring within seconds to minutes of reperfusion could result in reversible and irreversible damage to endothelial cells and other cells constituting the ischemic-reperfused organ matrix.

Peripheral vascular disease (PVD) is a common disease caused by atherosclerotic narrowing of the arteries of the lower extremities (Cooke, J. P., et al., *Vasc. Med.* 2:227–230 (1997); Brass, E. P. et al., *Vasc. Med.* 5:55–59 (2000); Hiatt, W. R., et al., *IJCP Suppl.* 119:20–27 (2001)). This disease affects 5% of all men and 2.5% of all women over the age of 60 in America (Weitz, J. I., et al., *Circulation* 94:3026–3049 (1996); Dawson, D. L. et al., *Am. J. Med.* 109:523–530 (2000)). In the United States, the prevalence of PVD is approximately 3 million and the incidence is 1 million new cases/year. Thus, the prevalence of this disease is increasing and will continue to increase as the population ages (Weitz, J. I. et al., supra).

Risk factors associated with PVD include age, hypertension, hyperlipidemia, hyperhomocysteinemia, hyperinsulinemia, insulin resistance, impaired glucose tolerance, smoking and diabetes mellitus. Of these, smoking and diabetes mellitus exhibit the strongest positive relationship to PVD.

Approximately a third of all patients diagnosed with PVD exhibit intermittent claudication, defined as lower extremity pain, muscle ache or muscle fatigue that is usually precipitated by exertion (Wood, A. J. J. et al., *N. Engl. J. Med.* 344:1608–1621 (2001)). Intermittent claudication results from ischemic disease of skeletal muscle characterized by repeated bouts of ischemia-reperfusion. In many ways, intermittent claudication resembles angina. In fact, patients presenting with intermittent claudication have a 3-fold higher incidence of cardiovascular mortality, and as many as 10% have co-existing cerebrovascular disease and 28% exhibit symptoms of coronary artery disease.

The all-cause, 5-year mortality in patients with intermittent claudication is 30% and if complicated by concomitant coronary artery disease, the mortality is 40%. The most serious complication of severe intermittent claudication is amputation of the affected limb, which is necessary in about 5% of all patients. Most often, amputation is required when non-healing ischemic ulcers on the affected limb become infected and/or gangrene occurs.

An underlying metabolic disorder of energy generation develops in ischemic skeletal muscle, which is not affected by revascularization or vasodilating agents. During normal aerobic metabolism, muscle tissue utilizes free fatty acids (FFA) to generate energy. During ischemia, the muscle switches to anaerobic metabolism, where glucose becomes the primary source of energy. Glucose oxidation consumes less energy than FFA oxidation, and hence glucose oxidation increases muscle efficiency during ischemia. However, the switch to glucose metabolism during ischemia is usually incomplete and some FFAs are utilized as a source of energy. This is due to the fact that glycolysis is inhibited in the presence of insulin resistance and high glucagon levels. In particular, excess blood FFA oxidation creates highly toxic free radicals that cause muscle tissue damage.

During ischemia, anaerobic glycolysis is an important source of ATP. Under these circumstances, glycogen is depleted and lactic acid accumulates. In low flow ischemia, such as occurs with narrowing of blood vessels to the lower extremities, the efficiency of ATP production is especially critical. In such an ischemic condition, the supply of oxygenated blood is limited but not absent, as may occur with thrombosis of a blood vessel resulting in complete obstruction. Fatty acid oxidation is inherently less efficient than glucose oxidation as a process for generating ATP. In fact, 8 to 50% more molecular oxygen is required to produce one molecule of ATP when fatty acids are used as the fuel source. Thus, in the setting of reduced blood flow, where oxygen delivery is limited, a more efficient means of producing ATP is glucose oxidation. Insulin promotes glucose oxidation and reduces fatty acid oxidation by activating pyruvate dehydrogenase (PDH), by enhancing glucose transport into muscle and by inhibiting fatty acid oxidation. The therapeutic benefit of administering insulin with glucose to patients suffering from muscle ischemia has been demonstrated in both animals and humans. However, this combination therapy creates an imbalance between blood glucose and insulin levels causing the patients to become hyperglycemic or hypoglycemic. These major adverse effects limit the utility of glucose plus insulin as a therapeutic combination.

As a side product of normal aerobic respiration, electrons are routinely lost from the mitochondrial electron transport chain. Such electrons react with molecular oxygen to generate the reactive free radical superoxide, which through a series of reaction steps, in the presence of hydrogen peroxide and iron, produces the extraordinarily reactive and toxic hydroxyl radical. Metabolically active aerobic tissues possess defense mechanisms including superoxide dismutase (SOD), which removes the free superoxide anion radical $O_2^-$; catalase, which degrades hydrogen peroxide; and glutathione, which scavenges free radicals; all of which are dedicated to degrading toxic free radicals. In the absence of such defense mechanisms these reactive oxygen species interact with cellular organelles, enzymes, or DNA, ultimately causing cell death.

A complex series of events occurs during ischemia and subsequent reperfusion of metabolic tissue. During the ischemic period, intracellular anti-oxidant enzyme activity, including that of SOD, catalase, and glutathione, decreases with a concomitant increase in xanthine oxidase activity in vascular endothelial tissue. The combination of an enhanced ability to produce oxygen free radicals (via enhanced xanthine oxidase activity) and reduced ability to scavenge the same oxygen radicals (via reduced SOD, catalase, and glutathione activity) greatly sensitizes the ischemic cell to an oxidative burst. Reperfusion of the tissue results in an oxidative burst within seconds to minutes of the reperfusion. The oxidative burst can result in damage to endothelial cells and other cells constituting the ischemic-reperfused tissue.

Attendant with the initial oxidative burst is oxidation damage to cell membranes. Lipid oxidation in cell membranes causes neutrophil chemotaxis to post-ischemic areas. Such activated neutrophils adhere to the vascular endothelium, induce the conversion of xanthine dehydrogenase to xanthine oxidase within the endothelial cells, and further aggravate the loss of endothelial integrity. Activated neutrophils also migrate out of the vasculature where they can directly kill myocytes.

Additional consequences of ischemia-reperfusion include reversible skeletal muscle dysfunction resulting from perturbations in normal calcium mobilization from the sarcoplasmic reticulum.

The paradox of cellular damage associated with a limited period of ischemic anoxia followed by reperfusion is that cell damage and death appear not only to directly result from the period of oxygen deprivation but also as a consequence of re-oxygenating the tissues. Reperfusion damage commences with the initial oxidative burst immediately upon reflow and worsens over a number of hours as inflammatory processes develop in the same post-ischemic tissues. Efforts dedicated to decreasing sensitivity of post-anoxic cells to oxidative damage and, additionally, efforts to reduce inflammatory responses in these same tissues have been shown to reduce the damage to post-anoxic reperfused tissue.

It, therefore, can be seen that there is a need for a safe effective composition having broad applicability to prevent or ameliorate the harmful effects of ischemia and reperfusion for tissues in general.

Three types of therapy for intermittent claudication are currently available, depending upon the severity and extent of the disease. For less severe cases, medical management consists of risk factor management, exercise training and chronic therapy with anti-platelet drugs (e.g., aspirin, ticlopidine, or clopidogrel) or vasodilators (e.g., pentoxifylline and cilostazol). Patients with more severe symptoms may undergo peripheral angioplasty or intravascular stent placement. Surgical revascularization is reserved for limb-threatening ischemia that is anatomically amenable to operation. Thus, there is a need for better methods for treating or preventing intermittent claudication.

SUMMARY OF THE INVENTION

Applicants have solved the above problem by discovering that glucagon-like peptide-1 (GLP-1) can be used to improve skeletal muscle performance by promoting glucose oxidation and reducing fatty acid oxidation.

The present invention relates to methods for treating or preventing intermittent claudication. In one embodiment, the method of this invention comprises administering to a subject a therapeutically effective amount of GLP-1 molecules. In another embodiment, the method comprises ameliorating, treating or preventing skeletal muscle injury caused by ischemia and/or reperfusion. In yet another embodiment, the method of the invention comprises promoting glucose transport into skeletal muscle. Individuals in need of treatment of ischemia and/or reperfusion are treated, preferably intravenously, with a composition which includes a compound which binds to a receptor for the glucagon-like peptide-1. Methods of the invention include a method for amelioration of skeletal muscle tissue injury caused by reperfusion of blood flow following a period of ischemia, comprising administering to an individual an effective amount of a composition including a compound that binds to a receptor for glucagon-like peptide-1. Compositions of the invention may include a pharmaceutically acceptable carrier selected from the group consisting of saline, buffered saline, dextrose, water, glycerol, ethanol, lactose, phosphate, mannitol, arginine, treholose, and combinations thereof.

DETAILED DESCRIPTION OF THE INVENTION

Unless defined otherwise, all technical and scientific terms used herein have the same meaning as commonly understood by one of ordinary skill in the art to which this invention belongs. In case of conflict, the present application including the definitions will control. All publications, patents and other references mentioned herein are incorporated by reference.

Although methods and materials similar or equivalent to those described herein can be used in the practice of testing of the present invention, suitable methods and materials are described below. The materials, methods and examples are for illustrative purposes only, and are not intended to be limiting. Other features and advantages of the invention will be apparent from the detailed description and from the claims.

Throughout this specification, the word "comprise" or variations such as "comprises" or "comprising" will be understood to imply the inclusion of a stated integer or groups of integers but not the exclusion of any other integer or group of integers.

In order to further define the invention, the following terms and definitions are herein provided.

The terms "GLP-1," "GLP-1 molecule," "glucagon-like peptide-1," or "glucagon-like peptide-1 molecule" according to this invention include GLP-1 as well as biologically active variants, analogs, mimetics, agonists, and derivatives thereof. "Biologically active" in this context means having the biological activity of GLP-1(7-36) amide (GLP-1(7-36) $NH_2$), but it is understood that the activity of the variant, analog, mimetic, agonist, or derivative thereof can be either less potent or more potent than native GLP-1(7-36)amide. The agonists of GLP-1, as well as GLP-1 mimetics that function as agonists, include, e.g., chemical compounds specifically designed to activate the GLP-1 receptor.

The term "glucagonostatic" as used herein, refers to an ability to inhibit the release of glucagon into the circulation.

The term "insulin regulating" as used herein, refers to an ability to control the release of insulin into the circulation, in relation to blood glucose and fatty acid levels.

The term "intermittent claudication" as used herein, refers to an ischemic disease of skeletal muscle characterized by repeated bouts of ischemia-reperfusion. Symptoms of intermittent claudication include pain, aching or fatigue that occurs in a muscle with an inadequate blood supply that is stressed by exercise.

The term "peripheral vascular disease" or "PVD" as used herein, refers to peripheral atherosclerotic disease or arteriosclerosis obliterans, which involves occlusion of the blood supply to the extremities by atherosclerotic plaques and encompasses intermittent claudication.

The term "pharmaceutically acceptable carrier or adjuvant" as used herein, refers to a non-toxic carrier or adjuvant that may be administered to a patient together with a compound of the invention, and which does not destroy the pharmacological activity thereof.

The terms "therapeutically or pharmaceutically effective" or "therapeutically or pharmaceutically effective amount" refers to an amount of the compound of this invention required to reduce or lessen the severity of intermittent claudication for some period of time. A therapeutically or pharmaceutically effective amount also means the amount required to improve the clinical symptoms.

The present invention relates to methods for treating intermittent claudication in a subject. The methods include administering to a subject a therapeutically effective amount of a GLP-1 molecule.

Glucagon-like Peptide-1 (GLP-1)

GLP-1 plays a key role in the regulation of plasma glucose homeostasis. It is involved in regulating insulin secretion in relation to blood glucose and/or lipid levels, and inhibiting glucagon release by the pancreas, inhibiting gastric acid secretion and motility, and suppressing appetite and food intake. GLP-1 is a member of the incretin group of secretagogue hormones that are released from the intestinal enteroendocrine cells in response to the ingestion of food. GLP-1 binds to the GLP-1 receptors, some of which are expressed on the β-cells of the pancreas. Binding of GLP-1 to its receptor triggers an intracellular signaling pathway that results in controlling insulin secretion with concomitant inhibition of glucagon production. This in turn leads to uptake of glucose in muscle and fat cells and the inhibition of hepatic glucose production, all of which lowers blood glucose levels. Inhibition of glucagon secretion also reduces systemic inflammation.

GLP-1 is a glucose-dependent insulinotropic hormone that effectively enhances peripheral glucose uptake without inducing dangerous hypoglycemia. Further, GLP-1 strongly suppresses glucagon secretion, independent of its insulin regulating action, and thereby reduces plasma free fatty acid (FFA) levels substantially more than can be accomplished with insulin alone. High FFA levels have been implicated as a major toxic mechanism during skeletal ischemia. Administered as a single agent or in combination with glucose, GLP-1 can provide protection for ischemic muscle tissue by acting like glucose-plus-insulin. However, GLP-1 has the distinct advantage of balancing blood glucose and insulin levels, thus, avoiding the risks of hyperglycemia and hypoglycemia. Therefore, it is both practical and feasible to treat ischemia with GLP-1 and obtain the benefits of a glucose-plus-insulin effect.

As used herein, a "GLP-1 molecule" includes the following compounds. Mammalian GLP peptides and glucagon are encoded by the same gene. In the ileum, the precursor is processed into two major classes of GLP peptide hormones, namely GLP-1 and GLP-2. GLP-1(1-37) has the sequence: His-Asp-Glu-Phe-Glu-Arg-His-Ala-Glu-Gly-Thr-Phe-Thr-Ser-Asp -Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO:1). GLP-1(1-37) is amidated post-translationally to yield GLP-1(1-36)$NH_2$, which has the sequence: His-Asp-Glu-Phe-Glu-Arg-His-Ala-Glu-Gly-Thr-Phe-Thr-Ser-Asp-Val-Ser -Ser-T-yr-Leu-Glu-Gly-Gln-Ala-Ala-Lys-Glu-Phe-Ile-Ala-Trp-Leu-Val-Lys-Gly-Arg($NH_2$) (SEQ ID NO: 2), or is enzymatically processed to yield GLP-1(7-37), which has the sequence: His-Ala -Glu-Gly-Thr-Phe-Thr-Ser-Asp-Val-Ser-Ser-Tyr-Leu-Glu-Gly-Gln-Ala-Ala-Lys-Glu-Phe-Ile-Ala -Trp-Leu-Val-Lys-Gly-Arg-Gly-(SEQ ID NO:3) GLP-1(7-37) can also be amidated to yield GLP-1(7-36)amide, which has the sequence: His-Ala-Glu-Gly-Thr-Phe-Thr-Ser-Asp-Val -Ser-Ser-Tyr-Leu-Glu-Gly-Gln-Ala-Ala-Lys-Glu-Phe-Ile-Ala-Trp-Leu-Val-Lys-Gly-Arg($NH_2$) (SEQ ID NO: 4). Likewise, GLP-1(1-36)amide can be processed to GLP-1(7-36)amide.

Intestinal L cells secrete GLP-1(7-37) (SEQ ID NO: 3) and GLP-1(7-36)$NH_2$ (SEQ ID NO: 4) in a ratio of 1:5. These truncated forms of GLP-1 have short half-lives in vivo (less than 10 minutes), and are inactivated by an aminodipeptidase (DPP IV) to yield GLP-1(9-37), which has the sequence: Glu-Gly-Thr-Phe-Thr-Ser-Asp-Val-Ser-Ser-Tyr-Leu -Glu-Gly-Gln-Ala-Ala-Lys-Glu-Phe-Ile-Ala-Trp-Leu-Val-Lys-Gly-Arg-Gly (SEQ ID NO: 5), and GLP-1(9-36)amide, which has the sequence: Glu-Gly-Thr-Phe-Thr-Ser-Asp-Val-Ser -Ser-Tyr-Leu-Glu-Gly-Gln-Ala-Ala-Lys-Glu-Phe-Ile-Ala-Trp-Leu-Val-Lys-Gly-Arg ($NH_2$) (SEQ ID NO:_6), respectively. It has been speculated that the peptides GLP-1(9-37) and GLP-1(9-36)amide might affect hepatic glucose production, but apparently they do not stimulate production or release of insulin from the pancreas.

As used in this specification, the term "GLP-1 molecule" includes GLP-1(1-37), GLP-1(1-36)$NH_2$, GLP-1(7-37), and GLP-1(7-36)$NH_2$ ("GLP-1(7-36)amide1") (collectively referred to as "GLP-1 peptides"). The present invention includes the use of recombinant human GLP-1 peptides and GLP-1 peptides derived from other species, whether recombinant or synthetic.

"GLP-1 molecule" further denotes biologically active variants, analogs, and derivatives of GLP-1 peptides. "Biologically active," in this context, means having GLP-1(7-36)

biological activity, but it is understood that the variant, analog, or derivative can be either less or more potent than GLP-1(7-36)amide, a native, biologically active form of GLP-1. See Göke & Byrne, *Diabetic Medicine.* 13; 854 (1996). GLP-1 molecules of the present invention also include polynucleotides that express agonists of GLP-1 (i.e., activators of the GLP-1 receptor molecule and its secondary messenger activity found on, inter alia, insulin-producing β-cells). GLP-1 mimetics that also are agonists of GLP-1 receptors include, for example, chemical compounds designed or anticipated to activate the GLP-1 receptor.

Included in GLP-1 molecules are any molecules, whether they be peptides, peptide mimetics, or other molecules, that bind to or activate a GLP-1 receptor, such as the GLP-1(7-36)amide receptor, and its second messenger cascade. GLP-1 molecules include species having insulin regulating activity and that are agonists of (i.e., activate), the GLP-1 receptor molecule and its second messenger activity on, inter alia, insulin producing β-cells.

"GLP-1 molecules" also include peptides that are encoded by polynucleotides that express biologically active GLP-1 variants, as defined herein. Also included in the present invention are GLP-1 molecules that are peptides containing one or more amino acid substitutions, additions or deletions, compared with GLP-1(7-36)amide. In one embodiment, the number of substitutions, deletions, or additions is 30 amino acids or less, 25 amino acids or less, 20 amino acids or less, 15 amino acids or less, 10 amino acids or less, 5 amino acids or less or any integer in between these amounts. In one aspect of the invention, the substitutions include one or more conservative substitutions. A "conservative" substitution denotes the replacement of an amino acid residue by another, biologically active similar residue. Examples of conservative substitutions include the substitution of one hydrophobic residue, such as isoleucine, valine, leucine, or methionine for another, or the substitution of one polar residue for another, such as the substitution of arginine for lysine, glutamic for aspartic acids, or glutamine for asparagine, and the like. The following table lists illustrative, but non-limiting, conservative amino acid substitutions.

| ORIGINAL RESIDUE | EXEMPLARY SUBSTITUTIONS |
| --- | --- |
| ALA | SER, THR |
| ARG | LYS |
| ASN | HIS, SER |
| ASP | GLU, ASN |
| CYS | SER |
| GLN | ASN, HIS |
| GLU | ASP, GLU |
| GLY | ALA, SER |
| HIS | ASN, GLN |
| ILE | LEU, VAL, THR |
| LEU | ILE, VAL |
| LYS | ARG, GLN, GLU, THR |
| MET | LEU, ILE, VAL |
| PHE | LEU, TYR |
| SER | THR, ALA, ASN |
| THR | SER, ALA |
| TRP | ARG, SER |
| TYR | PHE |
| VAL | ILE, LEU, ALA |
| PRO | ALA |

It is further understood that GLP-1 peptide variants include the above described peptides which have been chemically derivatized or altered, for example, peptides with non-natural amino acid residues (e.g., taurine, β- and γ-amino acid residues and D-amino acid residues), C-terminal functional group modifications, such as amides, esters, and C-terminal ketone modifications and N-terminal functional group modifications, such as acylated amines, Schiff bases, or cyclization, as found—for example—in the amino acid pyroglutamic acid.

Also included in the present invention are peptide sequences having greater than 50% sequence identity, and preferably greater than 90% sequence identity to (1) SEQ ID NOS:1, 2, 3,4; and (2) to truncated sequences thereof. As used herein, sequence identity refers to a comparison made between two molecules using standard algorithms well known in the art. The preferred algorithm for calculating sequence identity for the present invention is the Smith-Waterman algorithm, where SEQ ID NO:1 [i.e., GLP-1(1-37)] is used as the reference sequence to define the percentage identity of homologs over its length. The choice of parameter values for matches, mismatches, and insertions or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and −⅓ for a mismatched residue (a residue being either a single nucleotide or single amino acid). Waterman, *Bull. Math. Biol.* 46; 473 (1984). Insertions and deletions (indels), x, are weighted as $x_k=1+\frac{1}{3}k$, where k is the number of residues in a given insert or deletion. Id.

For instance, a sequence that is identical to the 37-amino acid residue sequence of SEQ ID NO: 1, except for 18 amino acid substitutions and an insertion of 3 amino acids, would have a percent identity given by:

[(1×37 matches)−(⅓×18 mismatches)−(1+3/3 indels)]/37=78% 'identity'

Also included in "GLP-1 molecules" of the present invention are six peptides in Gila monster venoms that are homologous to GLP-1. Their sequences are compared to the sequence of GLP-1 in Table 1.

TABLE 1

```
a.  H A E G T F T S D V S S Y L E G Q A A K E F I A W L V K G R (NH2)
b.  H S D G T F T S D L S K Q M E E E A V R L F I E W L K N G G P S S G A P P P S (NH2)
c.          D L S K Q M E E E A V R L F I E W L K N G G P S S G A P P P S (NH2)
d.  H G E G T F T S D L S K Q M E E E A V R L F I E W L K N G G P S S G A P P P S (NH2)
e.  H S D A T F T A E Y S K L L A K L A L Q K Y L E S I L G S S T S P R P P S S
f.  H S D A T F T A E Y S K L L A K L A L Q K Y L E S I L G S S T S P R P P S
```

TABLE 1-continued

```
g. H S D A I F T E E Y S K L L A K L A L Q K Y L A S I L G S R T S P P P (NH₂)
h. H S D A I F T Q Q Y S K L L A K L A L Q K Y L A S I L G S R T S P P P (NH₂)
``` a = GLP-1(7-36)amide (SEQ. ID NO:4)
b = exendin 3 (SEQ. ID NO:7).
c = exendin 4 (9-39(NH₂) (SEQ. ID NO:8).
d = exendin 4 (SEQ. ID NO:9).
e = helospectin I (SEQ. ID NO:10).
f = helospectin II (SEQ. ID NO:11).
g = helodermin (SEQ. ID NO:12).
h = $Q^8$, $Q^9$ helodermin (SEQ. ID NO:13).

Peptides (a, b, d, e, f, and g) are homologous at positions 1, 7, 11 and 18. GLP-1 and exendins are further homologous at positions, 4, 5, 6, 8, 9, 15, 22, 23, 25, 26 and 29. In position 2, A, S, and G are structurally similar. In position 3, residues D and E (Asp and Glu) are structurally similar. In positions 22 and 23, F (Phe) and I (Ile) are structurally similar to Y (Tyr) and L (Leu), respectively. Likewise, in position 26, L and I are structurally similar.

Thus, of the 30 residues of GLP-1, exendins 3 and 4 are identical in 15 positions and equivalent in 5 additional positions. The only positions where major structural changes are evident are at residues 16, 17, 19, 21, 24, 27, 28 and 30. Exendins also have 9 extra residues at the C-terminus.

Agonists of glucagon-like peptide that exhibit activity through the GLP-1(7-36)amide receptor have been described. See EP 0708179 A2; Hjorth et al., *J. Biol. Chem.* 269; 30121 (1994); Siegel et al., Amer. Diabetes Assoc. 57$^{th}$ Scientific Session, Boston (1997); Hareter et al., Amer. Diabetes Assoc. 57$^{th}$ Scientific Session, Boston (1997); Adelhorst et al., *J. Biol. Chem.* 269, 6275 (1994); Deacon et al., 16$^{th}$ International Diabetes Federation Congress Abstracts, *Diabetologia Supplement* (1997); Irwin et al., *Proc. Natl. Acad. Sci. USA* 94; 7915 (1997); Mojsov, *Int. J. Peptide Protein Res.* 40; 333 (1992); Göke & Byrne, *Diabetic Medicine* 13; 854 (1996). Recent publications disclose Black Widow GLP-1 and Ser$^2$ GLP-1. See Holz & Hakner, *Comp. Biochem. Physiol.*, Part B 121; 177 (1998) and Ritzel et al., *J. Endocrinol* 159; 93 (1998).

GLP-1 receptors are cell-surface proteins found, for example, on insulin-producing pancreatic β-cells; GLP-1(7-36) receptors and variants thereof have been characterised in the art. Methods of determining whether a chemical or peptide binds to or activates a GLP-1 receptor are known to the skilled artisan.

GLP-1 molecule biological activity can be determined by in vitro and in vivo animal models and human studies, as is well known to the skilled artisan. GLP-1 biological activity can be determined by standard methods, in general, by receptor-binding activity screening procedures, which involve providing appropriate cells that express the GLP-1 receptor on their surface, for example, insulinoma cell lines such as RINmSF cells or INS-1 cells. See Mojsov, *Int. J. Peptide Protein Res.* 40; 333 (1992) and EP 0708179 A2. Cells that are engineered to express a GLP-1 receptor also can be used. In addition to measuring specific binding of tracer to membrane using radioimmunoassay methods, cAMP activity or glucose dependent insulin production can also be measured. In one method, a polynucleotide encoding the GLP-1 receptor is employed to transfect cells so that they express the GLP-1 receptor protein. Thus, for example, these methods may be employed for screening for a receptor agonist by contacting such cells with compounds to be screened and determining whether such compounds generate a signal (i.e., activate the receptor). Other screening techniques include the use of cells that express the GLP-1 receptor, for example, transfected CHO cells, in a system to measure extracellular pH or ionic changes caused by receptor activation. For example, potential agonists may be contacted with a cell that expresses the GLP-1 receptor and a second messenger response (e.g., signal transduction or ionic or pH changes), may be measured to determine whether the potential agonist is effective.

Polyclonal and monoclonal antibodies can be utilized to detect, purify, and identify GLP-1-like peptides for use in the methods described herein. Antibodies such as ABGA1178 detect intact GLP-1(1-37) or N-terminally-truncated GLP-1(7-37) or GLP-1(7-36)amide. Other antibodies detect the end of the C-terminus of the precursor molecule, a procedure that allows one-by subtraction-to calculate the amount of biologically active, truncated peptide (i.e., GLP-1(7-37) amide). Orskov et al., *Diabetes* 42; 658 (1993); Orskov et al., *J. Clin. Invest.* 1991, 87; 415 (1991).

The GLP-1 molecules of the invention that are peptides that can be made by solid-state chemical peptide synthesis. Such peptides can also be made by conventional recombinant techniques using standard procedures described in, for example, Sambrook & Maniatis. "Recombinant," as used herein, means that a gene is derived from a recombinant (e.g., microbial or mammalian) expression system that has been genetically modified to contain a polynucleotide encoding a GLP-1 molecule as described herein.

The GLP-1 molecule peptides of the present invention may be a naturally purified product, or a product of synthetic chemical procedures, or produced by recombinant techniques from prokaryotic or eukaryotic hosts (for example, by bacteria, yeast, higher plant, insect, or mammalian cells in culture or in vivo). Depending on the host employed in a recombinant production procedure, the polypeptides of the present invention are generally non-glycosylated, but may be glycosylated.

The GLP-1 like peptides can be recovered and purified from recombinant cell cultures by methods including, but not limited to, ammonium sulfate or ethanol precipitation, acid extraction, anion or cation exchange chromatography, phosphocellulose chromatography, hydrophobic interaction chromatography, affinity chromatography, hydroxyapatite chromatography, and lectin chromatography. High-performance liquid chromatography (HPLC) can be employed for purification steps.

Particularly preferred GLP-1 molecules of the invention are GLP-1(7-36)amide, GLP-1(7-37), and exendin-4.

Uses for GLP-1

The dual capacity of GLP-1 to powerfully control insulin release and inhibit glucagon secretion, together with the strict glucose-dependence of its insulin regulating action, endow this molecule with a unique therapeutic potential in the management of ischemia-reperfusion such as that underlying intermittent claudication.

First, GLP-1 strongly regulates the secretion of endogenous insulin and, therefore, can be used to achieve all of the beneficial actions attributed to an insulin infusion in the metabolic treatment of ischemia-reperfusion.

Second, GLP-1 exerts a powerful glucagonostatic effect, which together with its insulin regulating action will lead to a strong suppression of FFAs. One of the major benefits of glucose-insulin treatments is the reduction in circulating FFA levels and the suppression of FFA uptake. FFAs and their metabolites have direct toxic effects on ischemic tissue as well as during the reperfusion period. Therefore, reduction of FFA levels is a major therapeutic goal of metabolic intervention in ischemia-reperfusion. As glucagon is a powerful stimulus for adipose tissue lipolysis and FFA production, GLP-1 mediated glucagon suppression further augments the insulin-induced reduction in circulating FFAs. Thus, the present invention provides methods of treating or preventing intermittent claudication in a subject comprising administering a therapeutically effective amount of GLP-1 molecules.

In another embodiment, the present invention provides a method of treating or preventing skeletal muscle injury caused by ischemia and/or reperfusion.

In yet another embodiment, the present invention provides a method of promoting glucose transport into skeletal muscle.

Also contemplated are methods of the present invention comprising additionally administering with GLP-1 molecules, free radical scavengers, which further decrease the risk of reperfusion damage. Such free radical scavengers include, e.g., glutathione, melatonin, vitamin E and superoxide dismutase (SOD).

GLP-1 should be effective in the majority of subjects without requiring concurrent glucose administration. However, a small proportion of subjects may require administration of both glucose and GLP-1 to elicit an adequate insulin response. In addition, it also may be necessary to administer potassium to correct excess shifts of potassium in the intracellular compartment when glucose is administered with GLP-1 molecules.

The free radical scavengers, glucose and/or potassium may be administered to a subject in need thereof simultaneously with the GLP-1 molecules. Alternatively, administration may occur at any other time during treatment of the subject with the GLP-1 molecules of this invention.

In a preferred embodiment, the subject to be treated is a mammal. e.g., dog, cat, rodent, etc. In a more preferred embodiment, the subject is a human.

Pharmaceutical Compositions

The GLP-1 molecules may be formulated into pharmaceutical compositions for administration to subjects, including humans. These pharmaceutical compositions, preferably include an amount of GLP-1 effective to treat or prevent intermittent claudication and a pharmaceutically acceptable carrier.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered by infusion or subcutaneous injection of a slow-release formulation.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered once a day or on an "as needed" basis.

The pharmaceutical compositions of this invention may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of GLP-1 molecule that may be combined with the carrier materials to produce a single dosage form will vary depending upon the host treated and the particular mode of administration. The compositions can be formulated so that a dosage of between 0.1–1000 pmoles/kg body weight/minute (when administered by infusion) of GLP-1 molecule is administered to a patient receiving these compositions. In some embodiments of the invention, the dosage is 0.1–10 pmoles/kg body weight/minute when administered by infusion). In a preferred embodiment, the dosage is 0.5–2.0 pmoles/kg/min/when administered by intravenous infusion. The composition may be administered as a single dose, multiple doses or over an established period of time in an infusion.

In a preferred embodiment, GLP-1 is administered to patients with confirmed peripheral vascular disease and intermittent claudication. In another preferred embodiment, GLP-1 is administered by injection at least once a day or by continuous infusion via pump. In yet another preferred embodiment, GLP-1 is formulated for administration from a subcutaneous depot over a period of days to weeks, oral administration or by intermittent inhalation.

A specific dosage and treatment regimen for any particular patient will depend upon a variety of factors, including the particular GLP-1 molecule, the patient's age, body weight, general health, gender, and diet, and the time of administration, rate of excretion, drug combination, and the severity of the particular disease being treated. Judgment of such factors by medical caregivers is within ordinary skill in the art. The amount of GLP-1 molecule will also depend on the individual patient to be treated, the route of administration, the type of formulation, the characteristics of the compound used, the severity of the disease, and the desired effect. The amounts of GLP-1 molecules can be determined by pharmacological and pharmacokinetic principles well-known in the art.

In order that the invention described herein may be more fully understood, the following examples are set forth. It should be understood that these examples are for illustrative purposes only and are not to be construed as limiting this invention in any manner.

EXAMPLES

Effect of GLP-1 on Cardiac Muscle Ischemia and Reperfusion in Rats

Wistar rats were anesthetized with thiopentone sodium. The left anterior descending (LAD) coronary artery was occluded. After 25 minutes of occlusion, reperfusion was allowed for 2 hours. This animal model has been described previously. Zacharowski, et al. (199) Br. J. Pharmacol. 128, 945–952.

GLP-1 (1.5 microgram/kg/min) was infused into anesthetized rats (n=10), commencing 10 minutes prior to reperfusion and continuing throughout the 2-hour reperfusion. Controls were sham operated with no occlusion (n=7), LAD occlusion+reperfusion+administration of saline (n=12), and LAD occlusion and reperfusion with vehicle (10 mM sodium acetate, 5.05% D-mannitol, pH 4.5, 1.5 mL/kg/hour; n=10).

Following reperfusion, the coronary artery was reoccluded, and Evans Blue dye (4 ml, 2% w/v) was injected into the left ventricle of the heart via a right carotid artery cannula. Evans Blue stains the perfused myocardium, while the occluded vascular bed remains uncolored. Animals were euthanized by anesthetic overdose and the hearts were removed for examination. Hearts were sectioned and the right ventricular wall was removed. The area at risk (pink) was separated from the non-ischemic tissue (blue). The area at risk (pink) was then cut into smaller pieces and stained with p-nitroblue tetrazolium (NBT; 0.5 mg/ml) for 20 min. at 37° C. In the presence of intact dehydrogenase enzyme systems (viable myocardium), NBT forms a dark blue compound. Areas of necrosis lack the enzyme and remain unstained. Tissue was separated according to staining and weighed to determine infarct size as a percentage of the area at risk.

In rats receiving the saline infusion, the infarct size was 50+/–3% of the area at risk. In rats receiving the vehicle infusion, the infarct size was 46+/–4% of the area at risk. In rats receiving the GLP-1 infusion, the infarct size was 31+/–4% of the area at risk. When compared with the vehicle group, infusion of GLP-1 caused a statistically significant (p<0.05) reduction in infarct size of approximately 33%. Thus, the systemic administration of GLP-1 can reduce myocardial infarct size even when administered after occlusion of a coronary artery and prior to onset of reperfusion. The results also indicate that the rats have significantly improved hemodynamics.

Effect of GLP-1 on Cardiac Muscle Ischemia and Reperfusion in Dogs

Two dogs were studied at baseline before, during, and for 6 hours after a 10-minute complete left circumflex coronary (LCx) occlusion. Each dog underwent occlusion/reperfusion in the presence and absence of GLP-1 infusion for 24 hours, beginning 1 minute prior to reperfusion.

GLP-1 infusion enhanced the recovery of ventricular wall regional dysfunction following 10 minutes of coronary artery occlusion. The results demonstrated that after a period of subcritical ischemia, administration of GLP-1 during reperfusion significantly reduced the stunning period. The results also demonstrated that the recovery after ischemia and the reduced stunning in the presence of GLP-1 were not due to increased coronary flow compared to controls, but rather due to favorable changes in myocardial muscle energetics.

Treatment of Human Patients with GLP-1

Patients will be selected for therapy with GLP-1 based on their presentation of the typical symptoms of intermittent claudication including but not limited to reversible leg pain that is elicited by walking and relieved by rest. The existence of peripheral arterial disease as the underlying cause of the claudication will be substantiated by hemodynamic measurements, such as the ABI (i.e. ankle/brachial pressure index<0.9). Moreover, the location of the lesion will be confirmed by duplex sonography or angiography.

Patients with confirmed peripheral vascular disease and intermittent claudication will be treated with GLP-1. GLP-1 will be administered by injection once or more each day or by continuous infusion via pump, which delivers a steady amount of drug. Alternatively, GLP-1 will be formulated for administration from a subcutaneous depot over days to weeks, by intermittent inhalation or orally.

Irrespective of the mode of administration, the total amount of GLP-1 delivered into the blood of a patient with intermittent claudication will be in the range of 720 to 2880 picomoles/kg/day. This is equivalent to 0.5–2.0 pmoles/kg/min administered by intravenous infusion.

The efficacy of GLP-1 will monitored by absolute claudication distance (ACD), which is measured on a treadmill at constant or graded workload. The ACD should increase for patients treated with GLP-1. The dose of GLP-1 may be adjusted (e.g. increased) to improve ACD.

We claim:

1. A method of treating or preventing intermittent claudication in a subject comprising the step of administering a therapeutically effective amount of a molecule selected from the group consisting of a glucagon-like peptide-1 (GLP-1), a biologically active fragment thereof having at least one of the following functions: regulating insulin secretion, inhibiting glucagon release, inhibiting gastric acid secretion, inhibiting gastric motility, suppressing food intake, enhancing peripheral glucose uptake, or, reducing circulating fatty acid levels, a GLP-1 receptor agonist, and an exendin.

2. A method of treating or preventing skeletal muscle injury caused by ischemia and/or reperfusion in a subject comprising the step of administering a therapeutically effective amount of a molecule selected from the group consisting of a GLP-1, a biologically active fragment thereof having at least one of the following functions: regulating insulin secretion, inhibiting glucagon release, inhibiting gastric acid secretion, inhibiting gastric motility, suppressing food intake, enhancing peripheral glucose uptake, or, reducing circulating fatty acids levels a GLP-1 receptor agonist, and an exendin.

3. The method according to claim 1 or 2, wherein the molecule is selected from the group consisting of GLP-1(7-36)NH$_2$ (SEQ ID NO:4), GLP-1(7-37), exendin-3 and exendin-4.

4. The method according to claim 1 or 2 wherein the GLP-1 molecule is selected from the group consisting of GLP-1(7-36)NH$_2$ (SEQ ID NO:4) and GLP-1(9-36)NH$_2$ (SEQ ID NO:6).

5. The method according to claim 1 or 2, wherein the subject is also administered free radical scavengers.

6. The method according to claim 5, wherein the free radical scavenger is selected from the group consisting of glutathione, melatonin, Vitamin E, and superoxide dismutase.

7. The method according to claim 1 or 2, wherein the subject is also administered glucose.

8. The method according to claim 7, wherein the subject is also administered potassium.

9. The method according to claim 1 or 2, wherein the subject is suffering from Peripheral Vascular Disease (PVD).

10. The method according to claim 1 or 2, wherein the subject is human.

11. The method according the claim 1 or 2, wherein the molecule is administered by an infusion pump or by subcutaneous injection of a slow release formulation of the molecule.

* * * * *

```
                       SEQUENCE LISTING

<160> NUMBER OF SEQ ID NOS: 13

<210> SEQ ID NO 1
<211> LENGTH: 37
<212> TYPE: PRT
<213> ORGANISM: mammalian

<400> SEQUENCE: 1

His Asp Glu Phe Glu Arg His Ala Glu Gly Thr Phe Thr Ser Asp Val
1               5                  10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 36
<212> TYPE: PRT
<213> ORGANISM: mammalian

<400> SEQUENCE: 2

His Asp Glu Phe Glu Arg His Ala Glu Gly Thr Phe Thr Ser Asp Val
1               5                  10                  15

Ser Ser Tyr Leu Glu Gly Gln Ala Ala Lys Glu Phe Ile Ala Trp Leu
            20                  25                  30

Val Lys Gly Arg
        35

<210> SEQ ID NO 3
<211> LENGTH: 31
<212> TYPE: PRT
<213> ORGANISM: mammalian

<400> SEQUENCE: 3

His Ala Glu Gly Thr Phe Thr Ser Asp Val Ser Ser Tyr Leu Glu Gly
1               5                  10                  15

Gln Ala Ala Lys Glu Phe Ile Ala Trp Leu Val Lys Gly Arg Gly
            20                  25                  30
```

<210> SEQ ID NO 4
<211> LENGTH: 30
<212> TYPE: PRT
<213> ORGANISM: mammalian

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 29
<212> TYPE: PRT
<213> ORGANISM: mammalian

<400> SEQUENCE: 5

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg Gly
            20                  25

<210> SEQ ID NO 6
<211> LENGTH: 28
<212> TYPE: PRT
<213> ORGANISM: mammalian

<400> SEQUENCE: 6

Glu Gly Thr Phe Thr Ser Asp Val Ser Ser Tyr Leu Glu Gly Gln Ala
1               5                   10                  15

Ala Lys Glu Phe Ile Ala Trp Leu Val Lys Gly Arg
            20                  25

<210> SEQ ID NO 7
<211> LENGTH: 39
<212> TYPE: PRT
<213> ORGANISM: Gila Monster venom

<400> SEQUENCE: 7

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 8
<211> LENGTH: 31
<212> TYPE: PRT
<213> ORGANISM: Gila Monster venom

<400> SEQUENCE: 8

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 9
<211> LENGTH: 39
<212> TYPE: PRT
<213> ORGANISM: Gila Monster venom

```
<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 11
<211> LENGTH: 38
<212> TYPE: PRT
<213> ORGANISM: Gila Monster venom

<400> SEQUENCE: 10

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
        35

<210> SEQ ID NO 11
<211> LENGTH: 37
<212> TYPE: PRT
<213> ORGANISM: Gila Monster venom

<400> SEQUENCE: 11

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser
        35

<210> SEQ ID NO 12
<211> LENGTH: 35
<212> TYPE: PRT
<213> ORGANISM: Gila Monster venom

<400> SEQUENCE: 12

His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35

<210> SEQ ID NO 13
<211> LENGTH: 35
<212> TYPE: PRT
<213> ORGANISM: Gila Monster venom

<400> SEQUENCE: 13

His Ser Asp Ala Ile Phe Thr Gln Gln Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35
```